United States Patent
Eyring et al.

(10) Patent No.: US 9,558,642 B2
(45) Date of Patent: Jan. 31, 2017

(54) SLEEP STATE MONITORING

(71) Applicant: Vivint, Inc., Provo, UT (US)

(72) Inventors: Matthew J. Eyring, Provo, UT (US); Jeremy B. Warren, Draper, UT (US); James Ellis Nye, Alpine, UT (US)

(73) Assignee: Vivint, Inc., Provo, UT (US)

( * ) Notice: Subject to any disclaimer, the term of this patent is extended or adjusted under 35 U.S.C. 154(b) by 0 days.

(21) Appl. No.: 14/692,375

(22) Filed: Apr. 21, 2015

(65) Prior Publication Data

US 2016/0314673 A1 Oct. 27, 2016

(51) Int. Cl.
- *G08B 23/00* (2006.01)
- *G08B 21/06* (2006.01)
- *A61B 5/00* (2006.01)
- *A61M 21/02* (2006.01)

(52) U.S. Cl.
CPC ............. *G08B 21/06* (2013.01); *A61B 5/4812* (2013.01); *A61B 5/746* (2013.01); *A61M 21/02* (2013.01)

(58) Field of Classification Search
CPC ............ G08B 21/0208; G08B 21/0225; A47D 15/003; A47D 15/008; A61B 2503/04; A61B 5/0002; A61B 5/11; A61B 5/4809; A61B 5/4812
See application file for complete search history.

(56) References Cited

U.S. PATENT DOCUMENTS

| | | | |
|---|---|---|---|
| 5,479,932 A | 1/1996 | Higgins et al. | |
| 5,505,199 A * | 4/1996 | Kim | A61B 5/11 348/143 |
| 7,774,052 B2 * | 8/2010 | Burton | A61B 5/0476 600/544 |
| 2005/0119532 A1 | 6/2005 | Cloutier | |
| 2005/0210592 A1 * | 9/2005 | Littlehorn | A47D 15/008 5/655 |
| 2010/0026798 A1 * | 2/2010 | Schmid | A61B 5/0002 348/61 |
| 2012/0059927 A1 | 3/2012 | Schieffelin et al. | |
| 2013/0084551 A1 * | 4/2013 | Houston | G09B 5/04 434/319 |
| 2014/0055263 A1 | 2/2014 | Witt et al. | |
| 2015/0105608 A1 * | 4/2015 | Lipoma | A61B 5/6896 600/27 |

OTHER PUBLICATIONS

Withings Aura, obtained from http://www.withings.com/eu/withings-aura.html#, on Mar. 2, 2015.

* cited by examiner

*Primary Examiner* — Kerri McNally
*Assistant Examiner* — Renee Dorsey
(74) *Attorney, Agent, or Firm* — Holland & Hart LLP

(57) ABSTRACT

A method for operating a security and/or automation system is described. A sensor may identify when a first person is in a sleep state. The sensor may detect a disturbance in the sleep state, and alert a second person when the detected disturbance satisfies one or more disturbance parameters.

20 Claims, 8 Drawing Sheets

SLEEP STATE MONITORING

BACKGROUND

The present disclosure, for example, relates to security and/or automation systems, and more particularly to monitoring a person, sometimes a child, in the home environment.

Security and automation systems are widely deployed to provide various types of communication and functional features such as monitoring, communication, notification, and/or others. These systems may be capable of supporting communication with a user through a communication connection or a system management action.

Managing the status of a person in a household can be a complicated process. Depending on the age of the person, multiple factors may need to be tracked and monitored for a second person to feel the first person is adequately safe and healthy. Additionally, monitoring systems may be stand-alone systems not integrated into a more holistic approach to monitoring.

SUMMARY

Parents often wish to monitor their small children and create a healthy environment for their children. While monitors and other devices exist, the devices are stand alone and perform singular functions. The present systems and methods provide an overall monitoring system that may be linked to an automation system to provide a holistic approach to monitoring another person (e.g., a baby, an elderly person, etc).

In one embodiment, a method for operating a security and/or automation system is described. The method may comprise identifying, via a sensor, when a first person is in a sleep state, detecting, via the sensor, a disturbance in the sleep state, and alerting a second person when the detected disturbance satisfies one or more disturbance parameters.

In another embodiment, detecting a disturbance in the sleep state may further comprise audibly detecting, via the sensor, an audible indicator associated with the first person and starting a timer based at least in part on the audible detection. The time may be reset if the audible indicator ceases for a predetermined time duration. The second person may be alerted if the timer satisfies a predetermined time threshold. The method may further include determining when the audible indicator satisfies a predetermined decibel threshold and alerting the second person based at least in part on the determining.

In some embodiments, the method may include identifying a location of the first person and deactivating one or more household alerts based at least in part on the identified location. The method may include analyzing an acoustic signature of sounds associated with the first person. A state of the first person may be evaluated based at least in part on the analyzing. The second person may be alerted if the acoustic signature satisfies a signature parameter. The method may additionally include recording video data and audio data of the first person when the sleep state is disrupted, saving the video data and the audio data, and analyzing the video data and the audio data to identify a cause of the disturbance.

In some embodiments, the method may include tracking vital signs of the first person while the first person is in the sleep state and immediately alerting emergency personnel when at least one of the vital signs satisfies an emergency threshold. The method may include saving video data, audio data, and sensor information for a predetermined time period, the predetermined time period comprising a first time period before the emergency threshold is satisfied until a second time period after the emergency threshold is satisfied. In some instances, the method may include activating a soothing mechanism proximate a location of the first person when the sleep state is disturbed. Detecting a disturbance in the sleep state may further comprise detecting when a current state of the first person requires a change. The sensor may comprise at least one of a bed sensor, an audio sensor, a video sensor, a motion sensor, a camera, a microphone, a light sensor, or a combination thereof.

In further embodiments, an apparatus for security and/or automation systems is described. The apparatus may include a processor, memory in electronic communication with the processor, and instructions stored in the memory. The instructions may be executable by the processor to identify, via a sensor, when a first person is in a sleep state, detect, via the sensor, a disturbance in the sleep state, and alert a second person when the detected disturbance satisfies one or more disturbance parameters.

In still further embodiments, a non-transitory computer-readable medium storing computer-executable code is described. The code may be executable by a processor to identify, via a sensor, when a first person is in a sleep state, detect, via the sensor, a disturbance in the sleep state, and alert a second person when the detected disturbance satisfies one or more disturbance parameters.

The foregoing has outlined rather broadly the features and technical advantages of examples according to this disclosure so that the following detailed description may be better understood. Additional features and advantages will be described below. The conception and specific examples disclosed may be readily utilized as a basis for modifying or designing other structures for carrying out the same purposes of the present disclosure. Such equivalent constructions do not depart from the scope of the appended claims. Characteristics of the concepts disclosed herein—including their organization and method of operation—together with associated advantages will be better understood from the following description when considered in connection with the accompanying figures. Each of the figures is provided for the purpose of illustration and description only, and not as a definition of the limits of the claims.

BRIEF DESCRIPTION OF THE DRAWINGS

A further understanding of the nature and advantages of the present disclosure may be realized by reference to the following drawings. In the appended figures, similar components or features may have the same reference label. Further, various components of the same type may be distinguished by following a first reference label with a dash and a second label that may distinguish among the similar components. However, features discussed for various components—including those having a dash and a second reference label—apply to other similar components. If only the first reference label is used in the specification, the description is applicable to any one of the similar components having the same first reference label irrespective of the second reference label.

DETAILED DESCRIPTION

The methods and systems contained herein may be used to monitor other people requiring extra care, such as a disabled person, elderly person, sick person, or the like. One or more sensors may be proximate the person being monitored, either as a wearable device or proximate their location, such as next to a sleeping location. The sensors may track various biometric readings as well as environmental factors to monitor a state of the first person.

The following description provides examples and is not limiting of the scope, applicability, and/or examples set forth in the claims. Changes may be made in the function and/or arrangement of elements discussed without departing from the scope of the disclosure. Various examples may omit, substitute, and/or add various procedures and/or components as appropriate. For instance, the methods described may be performed in an order different from that described, and/or various steps may be added, omitted, and/or combined. Also, features described with respect to some examples may be combined in other examples.

Figure 1:
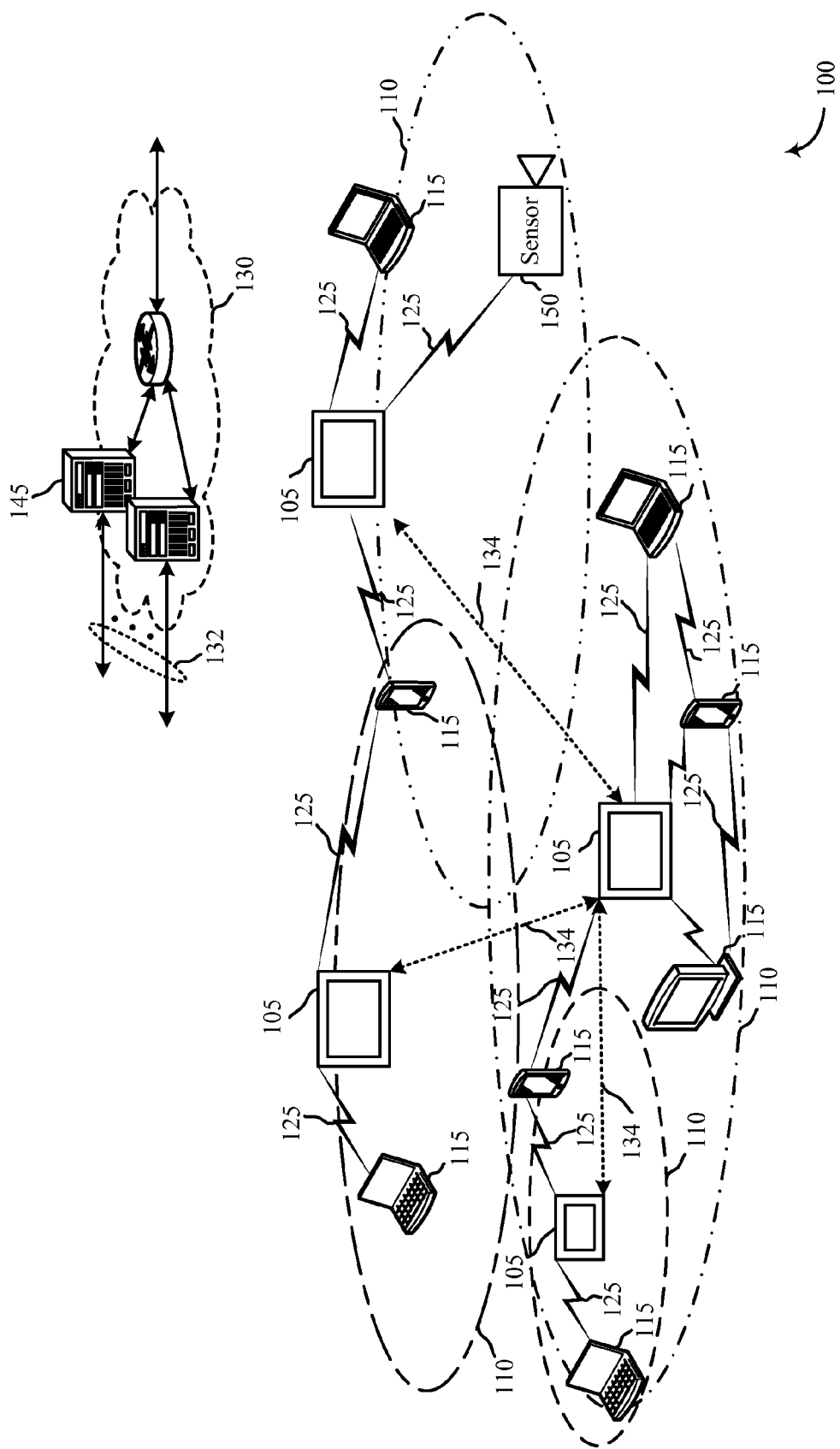
FIG. 1 shows a block diagram relating to a security and/or an automation system, in accordance with various aspects of this disclosure.

FIG. 1 illustrates an example of a communications system 100 in accordance with various aspects of the disclosure. The communications system 100 may include control panels 105, devices 115, a network 130, and/or sensors 150. The network 130 may provide user authentication, encryption, access authorization, tracking, Internet Protocol (IP) connectivity, and other access, calculation, modification, and/or functions. The control panels 105 may interface with the network 130 through a first set of wired and/or wireless communication links 132 to communicate with one or more remote servers 145. The control panels 105 may perform communication configuration, adjustment, and/or scheduling for communication with the devices 115, or may operate under the control of a controller. In various examples, the control panels 105 may communicate—either directly or indirectly (e.g., through network 130)—with each other over a second set of wired and/or wireless communication links 134. Control panels 105 may communicate with a back end server (such as the remote servers 145)—directly and/or indirectly—using the first set of one or more communication links 132.

The control panels 105 may wirelessly communicate with the devices 115 via one or more antennas. Each of the control panels 105 may provide communication coverage for a respective geographic coverage area 110. In some examples, control panels 105 may be referred to as a control device, a base transceiver station, a radio base station, an access point, a radio transceiver, or some other suitable terminology. The geographic coverage area 110 for a control panel 105 may be divided into sectors making up only a portion of the coverage area. The communications system 100 may include control panels 105 of different types. There may be overlapping geographic coverage areas 110 for one or more different parameters, including different technologies, features, subscriber preferences, hardware, software, technology, and/or methods. For example, each control panel 105 may be related to one or more discrete structures (e.g., a home, a business) and each of the one more discrete structures may be related to one or more discrete areas. In other examples, multiple control panels 105 may be related to the same one or more discrete structures (e.g., multiple control panels relating to a home and/or a business complex).

The devices 115 may be dispersed throughout the communications system 100 and each device 115 may be stationary and/or mobile. A device 115 may include a cellular phone, a personal digital assistant (PDA), a wireless modem, a wireless communication device, a handheld device, a tablet computer, a laptop computer, a cordless phone, a wireless local loop (WLL) station, a display device (e.g., TVs, computer monitors, etc.), a printer, a camera, and/or the like. A device 115 may also include or be referred to by those skilled in the art as a user device, a smartphone, a BLUETOOTH® device, a Wi-Fi device, a mobile station, a subscriber station, a mobile unit, a subscriber unit, a wireless unit, a remote unit, a mobile device, a wireless device, a wireless communications device, a remote device, an access terminal, a mobile terminal, a wireless terminal, a remote terminal, a handset, a user agent, a mobile client, a client, and/or some other suitable terminology.

The control panels 105 may wirelessly communicate with the sensors 150 via one or more antennas. The sensors 150 may be dispersed throughout the communications system 100 and each sensor 150 may be stationary and/or mobile. A sensor 150 may include and/or be one or more sensors that sense: proximity, motion, temperatures, humidity, sound level, smoke, structural features (e.g., glass breaking, window position, door position), time, light geo-location data of a user and/or a device, distance, biometrics, weight, speed, height, size, preferences, light, darkness, weather, time, system performance, and/or other inputs that relate to a security and/or an automation system. A device 115 and/or a sensor 150 may be able to communicate through one or more wired and/or wireless connections with various components such as control panels, base stations, and/or network equipment (e.g., servers, wireless communication points, etc.) and/or the like.

The communication links 125 shown in communications system 100 may include uplink (UL) transmissions from a device 115 to a control panel 105, and/or downlink (DL) transmissions, from a control panel 105 to a device 115. The downlink transmissions may also be called forward link transmissions while the uplink transmissions may also be called reverse link transmissions. Each communication link 125 may include one or more carriers, where each carrier may be a signal made up of multiple sub-carriers (e.g., waveform signals of different frequencies) modulated according to the various radio technologies. Each modulated signal may be sent on a different sub-carrier and may carry control information (e.g., reference signals, control channels, etc.), overhead information, user data, etc. The communication links 125 may transmit bidirectional communications and/or unidirectional communications. Communication links 125 may include one or more connections, including but not limited to, 345 MHz, Wi-Fi, BLUETOOTH®, BLUETOOTH® Low Energy, cellular, Z-WAVE®, 802.11, peer-to-peer, LAN, WLAN, Ethernet, fire wire, fiber optic, and/or other connection types related to security and/or automation systems.

In some embodiments, of communications system 100, control panels 105 and/or devices 115 may include one or more antennas for employing antenna diversity schemes to improve communication quality and reliability between control panels 105 and devices 115. Additionally or alternatively, control panels 105 and/or devices 115 may employ multiple-input, multiple-output (MIMO) techniques that may take advantage of multi-path, mesh-type environments to transmit multiple spatial layers carrying the same or different coded data.

While the devices 115 may communicate with each other through the control panel 105 using communication links 125, each device 115 may also communicate directly with one or more other devices via one or more direct communication links 134. Two or more devices 115 may communicate via a direct communication link 134 when both devices 115 are in the geographic coverage area 110 or when one or neither devices 115 is within the geographic coverage area 110. Examples of direct communication links 134 may include Wi-Fi Direct, BLUETOOTH®, wired, and/or, and other P2P group connections. The devices 115 in these examples may communicate according to the WLAN radio and baseband protocol including physical and MAC layers from IEEE 802.11, and its various versions including, but not limited to, 802.11b, 802.11g, 802.11a, 802.11n, 802.11ac, 802.11ad, 802.11ah, etc. In other implementations, other peer-to-peer connections and/or ad hoc networks may be implemented within communications system 100.

In some embodiments, the sensors 150 may be proximate a room for a person to the be monitored. If the person is a small child, the sensors 150 may be proximate a sleep location such as a crib.

Figure 2:
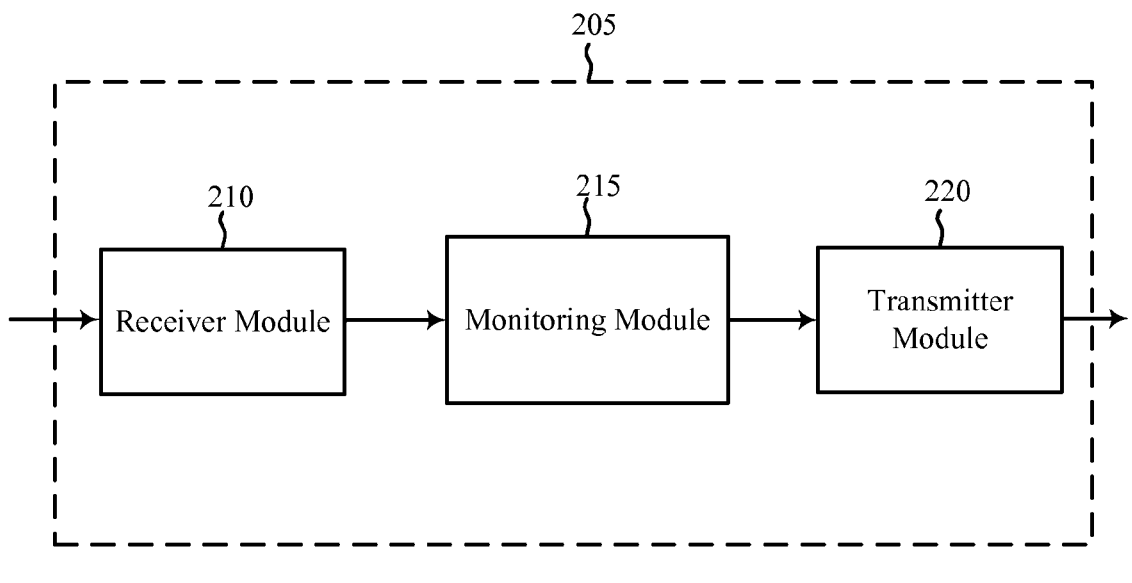
FIG. 2 shows a block diagram of a device relating to a security and/or an automation system, in accordance with various aspects of this disclosure.

FIG. 2 shows a block diagram 200 of an apparatus 205 for use in electronic communication, in accordance with various aspects of this disclosure. The apparatus 205 may be an example of one or more aspects of a control panel 105 described with reference to FIG. 1. The apparatus 205 may include a receiver module 210, a monitoring module 215, and/or a transmitter module 220. The apparatus 205 may also be or include a processor. Each of these modules may be in communication with each other—directly and/or indirectly.

The components of the apparatus 205 may, individually or collectively, be implemented using one or more application-specific integrated circuits (ASICs) adapted to perform some or all of the applicable functions in hardware. Alternatively, the functions may be performed by one or more other processing units (or cores), on one or more integrated circuits. In other examples, other types of integrated circuits may be used (e.g., Structured/Platform ASICs, Field Programmable Gate Arrays (FPGAs), and other Semi-Custom ICs), which may be programmed in any manner known in the art. The functions of each module may also be implemented—in whole or in part—with instructions embodied in a memory formatted to be executed by one or more general and/or application-specific processors.

The receiver module 210 may receive information such as packets, user data, and/or control information associated with various information channels (e.g., control channels, data channels, etc.). The receiver module 210 may be configured to receive information from sensors proximate a first person. Information may be passed on to the monitoring module 215, and to other components of the apparatus 205.

The monitoring module 215 may monitor aspects of a person such as a young child. In some instances, the monitoring may occur while an adult or supervisory person is not within a predetermined proximity of the person. In other embodiments, the monitoring may occur if one or more monitoring parameters are satisfied. The monitoring parameters may comprise location of child, monitoring set to an on position, potential health hazards detected, and the like. The monitoring module 215 may monitor the overall health and well-being of the child. For example, the monitoring module 215 may monitor breathing, defecating, feeding, temperature, distress state, and the like. One or more monitors may be proximate the child and/or a location associated with the child such as a crib, rocker, or the like. The sensors may detect information and supply the information to the monitoring module 215. The monitoring module 215 may extract and analyze the information before analyzing any actions to take based on the inputs received.

The transmitter module 220 may transmit the one or more signals received from other components of the apparatus 205. The transmitter module 220 may transmit data from the baby module to an end user. In some examples, the transmitter module 220 may be collocated with the receiver module 210 in a transceiver module.

Figure 3:
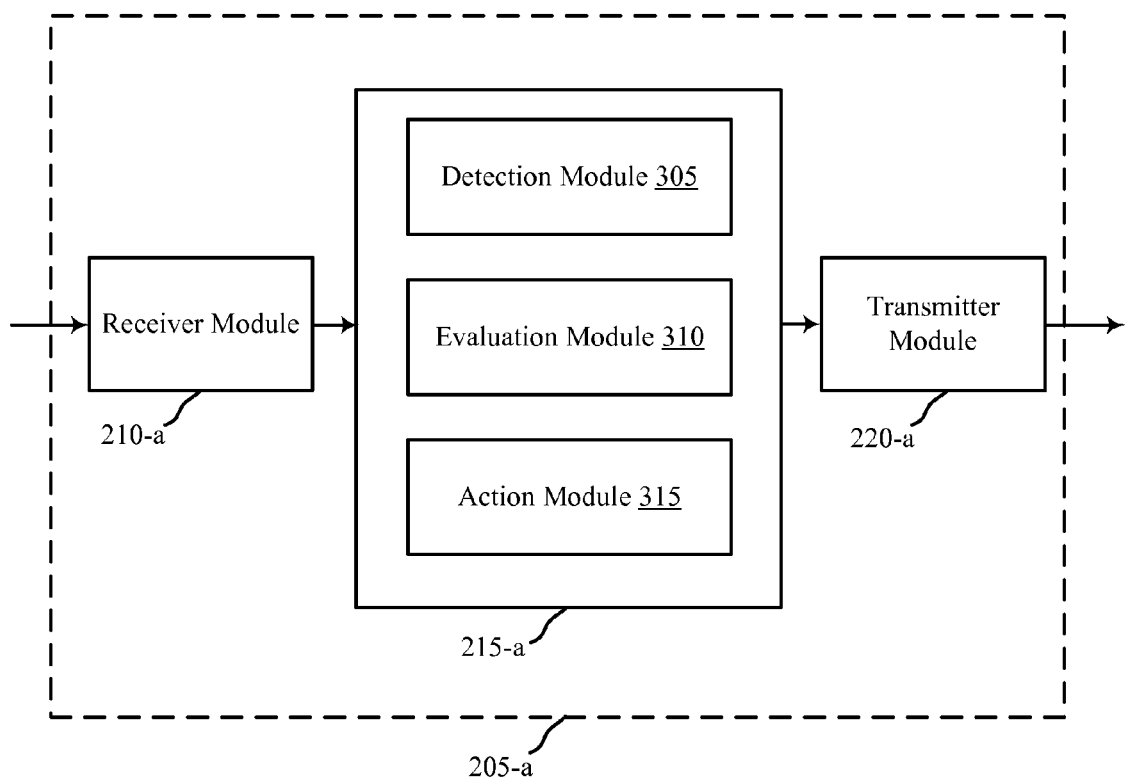
FIG. 3 shows a block diagram of a device relating to a security and/or an automation system, in accordance with various aspects of this disclosure.

FIG. 3 shows a block diagram 300 of an apparatus 205-a for use in wireless communication, in accordance with various examples. The apparatus 205-a may be an example of one or more aspects of a control panel 105 described with reference to FIG. 1. It may also be an example of an apparatus 205 described with reference to FIG. 2. The apparatus 205-a may include a receiver module 210-a, a monitoring module 215-a, and/or a transmitter module 220-a, which may be examples of the corresponding modules of apparatus 205. The apparatus 205-a may also include a processor. Each of these components may be in communication with each other. The monitoring module 215-a may include a detection module 305, an evaluation module 310, and an action module 315. The receiver module 210-a and the transmitter module 220-a may perform the functions of the receiver module 210 and the transmitter module 220, of FIG. 2, respectively.

The components of the apparatus 205-a may, individually or collectively, be implemented using one or more application-specific integrated circuits (ASICs) adapted to perform some or all of the applicable functions in hardware. Alternatively, the functions may be performed by one or more other processing units (or cores), on one or more integrated circuits. In other examples, other types of integrated circuits may be used (e.g., Structured/Platform ASICs, Field Programmable Gate Arrays (FPGAs), and other Semi-Custom ICs), which may be programmed in any manner known in the art. The functions of each module may also be implemented, in whole or in part, with instructions embodied in a memory, formatted to be executed by one or more general or application-specific processors.

The detection module 305 may use one or more sensors to detect the presence and/or the state of a first person. The presence may be a location of the first person such as a bassinet, crib, bed, and the like. The first person may be under an age threshold. For example, the first person may be an infant, toddler, child, or the like. One or more sensors may be proximate a child's bed. The bed may be a crib or may be a toddler bed or some other sleeping arrangements for a person. The sensors may comprise a microphone, video sensor, sleep sensor, biometric sensors, heart rate sensors, pulse sensors, bed sensor, audio sensor, motion sensor, light sensor, some combination thereof, and the like. The sensors may detect various levels of activity concerning the person. The audio sensor, microphone, and video may provide an audiovisual link to the person to allow a supervisory person to visually and audibly assess a situation.

The sensors may detect when a first person is in a sleep state. The first person may be a child. The sleep state may be the beginning stages of sleep or may be in a deep sleep. The sensors may determine the sleep state by detecting motion, heart rate, breathing patterns, and the like. If a first person has a steady heart-rate, even breathing, and is not moving, the detection module 305 may determine the first person is in a sleep state. The detection module 305 may track other vital signs of the first person while the first person is in the sleep state. For example, in addition to the heart rate and breathing pattern, the detection module 305 may track a pulse, brain activity, and the like.

The detection module 305 may monitor any disturbances in the sleep state. For example, the detection module 305 may continue to monitor the sleep state indicators to determine if any changes in the sleep state arise. If the detection module 305 detects a disturbance in the sleep state, the detection module 305 may record information prior to the detected disturbance and for a period of time after the detected disturbance. The recording may comprise audio and/or video information as well as sensor data pertinent to the first person.

The detection module 305 may audibly detect, via a sensor, an audible indicator associated with the first person. For example, a sensor may detect the first person is moving in the bed, crying, asking for help, and the like. The detection module 305 may continue to monitor the presence of the audible indicator. In some embodiments, the audible indicator may cease, indicating the first person has fallen back asleep. In another embodiment, the audible indicator may continue and, in some instances, may increase in decibel level. Therefore, the detection module 305 may determine when the audible indicator satisfies a predetermined decibel threshold. The predetermined decibel threshold may indicate the first person's distress and need for attention. The detection module 305 may detect and transmit the acoustic signature of sounds associated with the first person. The sounds may be similar to the audible indicator. The sounds may be emanating from the first person, such as crying, asking for help, screaming, and the like.

The evaluation module 310 may review the information from the detection module 305 to determine a potential state of the first person. The evaluation module 310 may stream the information from the detection module 305 into different software modules. The software modules may analyze the audiovisual data to discern different need states of the first person. The evaluation module 310 may be a learning module and may analyze acoustic signatures to discern different distress levels of a person to determine if the person requires attention. Likewise, the evaluation module 310 may review video data to determine when parental interaction is needed. This may comprise discerning between hungry cries, awake cries, upset cries, and the like. The evaluation module 310 may view video data and determine a child's legs have become tangled in crib slats and the child requires attention to disentangle. The video may ascertain an infant has come undone from a swaddle and may be upset. The child may also require a change, such as a diaper change or clothing change. The evaluation module 310 may additionally determine a discrepancy in health monitoring such as a lower heart rate or lack of breathing and may trigger an emergency response.

The evaluation module 310 may record video and audio data of the first person in various states. For example, the evaluation module 310 may record and save the audiovisual information when a sleep stated is disrupted. The evaluation module 310 may then evaluate the data to identify a cause of the disturbance. This may enable a caregiver to reduce potential disruptions to the first person's sleep state to ensure the first person achieves a more restful state. If the first person is a child, it may ensure the child's nap goes uninterrupted.

Similarly, if the vital signs satisfy an emergency threshold, the evaluation module 310 may save video, audio, and sensor information for a predetermined time period to evaluate a cause. The predetermined time period may comprise a first time period before the emergency threshold is satisfied until a second time period after the emergency threshold is satisfied. The emergency threshold may comprise vital signs not being within an acceptable range. For example, breathing, heart rate, and/or pulse may have slowed down or ceased. Brain activity may fall below an acceptable level. In some embodiments, extreme body temperatures may result in an emergency situation.

The action module 315 may take one or more actions based on the evaluation module 310. As mentioned, if the evaluation module 310 detects an emergency such as a lack of breathing, lower or lowering heart rate, or the like, the action module 315 may immediately alert emergency personnel and a supervisory person such as a parent. The alert to emergency personnel may contain the recorded data on the child and request emergency personnel at the location immediately. The alert to the supervisory personnel may include instructions of what to do with the baby, such as CPR or chest compressions, notify the supervisory personnel of the emergency personnel. If the supervisory personnel is not a parent, a parent may additionally be contacted. For example, the parents may be out and leave a caregiver to care for a child. Or the parents may be divorced and an alert may be sent to the parent not living at the current location of the child, and the like.

If the evaluation module 310 detects a non-emergency situation, the action module 315 may take different steps. If the person is a child and is stirring, the action module 315 may begin a timer and a decibel counter. The action module 315 may activate a soothing mechanism proximate the location of the child to attempt to lull the child to sleep. If the child continues to stir and cry after a predetermined period, an alert may be sent to a supervisory person. If the child's cries exceed a decibel threshold, the supervisory person may additionally be alerted. Alternatively, if the evaluation module 310 determines a distress state of the person, the action module 315 may take different actions. For example, the action module 315 may cause an alert to be sent to a supervisory person regarding the state of the person. The person, which may be a child, may require a feeding, detangling, may require more blankets or less blankets depending on temperature, may require a diaper change, or the like.

Figure 4:
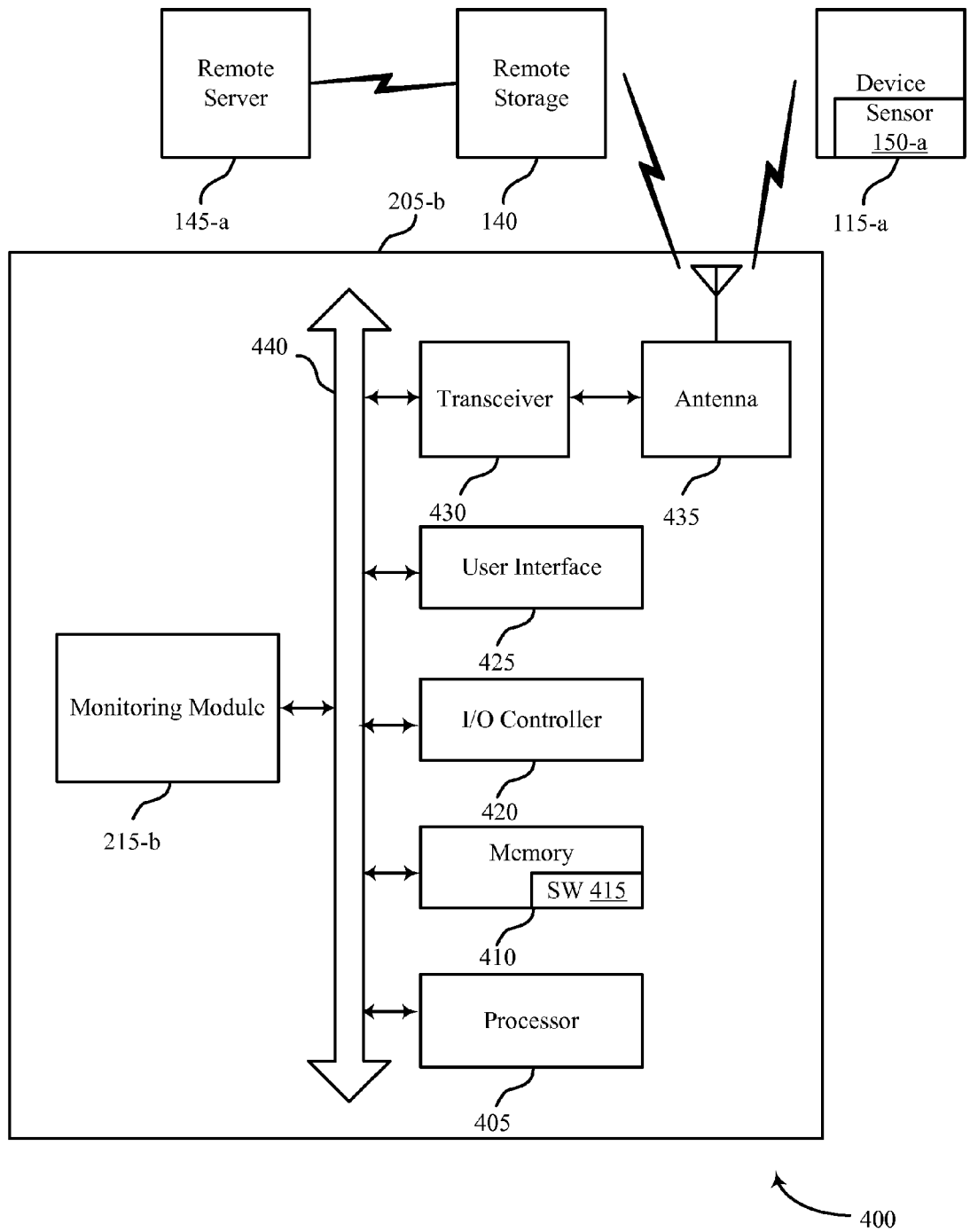
FIG. 4 shows a block diagram relating to a security and/or an automation system, in accordance with various aspects of this disclosure.

FIG. 4 shows a system 400 for use in monitoring the sleep state of persons systems, in accordance with various examples. System 400 may include an apparatus 205-*b*, which may be an example of the control panels 105 of FIG. 1. Apparatus 205-*b* may also be an example of one or more aspects of apparatus 205 and/or 205-*a* of FIGS. 2 and 3.

Apparatus 205-*b* may also include components for bi-directional voice and data communications including components for transmitting communications and components for receiving communications. For example, apparatus 205-*b* may communicate bi-directionally with one or more of device 115-*a*, one or more sensors 150-*a*, remote storage 140, and/or remote server 145-*a*, which may be an example of the remote server of FIG. 1. This bi-directional communication may be direct (e.g., apparatus 205-*b* communicating directly with remote storage 140) or indirect (e.g., apparatus 205-*b* communicating indirectly with remote server 145-*a* through remote storage 140).

Apparatus 205-*b* may also include a processor module 405, and memory 410 (including software/firmware code (SW) 415), an input/output controller module 420, a user interface module 425, a transceiver module 430, and one or more antennas 435 each of which may communicate—directly or indirectly—with one another (e.g., via one or more buses 440). The transceiver module 430 may communicate bi-directionally—via the one or more antennas 435, wired links, and/or wireless links—with one or more networks or remote devices as described above. For example, the transceiver module 430 may communicate bi-directionally with one or more of device 115-*a*, remote storage 140, and/or remote server 145-*a*. The transceiver module 430 may include a modem to modulate the packets and provide the modulated packets to the one or more antennas 435 for transmission, and to demodulate packets received from the one or more antennas 435. While an apparatus (e.g., 205-*b*) may include a single antenna 435, the apparatus may also have multiple antennas 435 capable of concurrently transmitting or receiving multiple wired and/or wireless transmissions. In some embodiments, one element of apparatus 205-*b* (e.g., one or more antennas 435, transceiver module 430, etc.) may provide a direct connection to a remote server 145-*a* via a direct network link to the Internet via a POP (point of presence). In some embodiments, one element of apparatus 205-*b* (e.g., one or more antennas 435, transceiver module 430, etc.) may provide a connection using wireless techniques, including digital cellular telephone connection, Cellular Digital Packet Data (CDPD) connection, digital satellite data connection, and/or another connection.

The signals associated with system 400 may include wireless communication signals such as radio frequency, electromagnetics, local area network (LAN), wide area network (WAN), virtual private network (VPN), wireless network (using 802.11, for example), 345 MHz, Z-WAVE®, cellular network (using 3G and/or LTE, for example), and/or other signals. The one or more antennas 435 and/or transceiver module 430 may include or be related to, but are not limited to, WWAN (GSM, CDMA, and WCDMA), WLAN (including BLUETOOTH® and Wi-Fi), WMAN (WiMAX), antennas for mobile communications, antennas for Wireless Personal Area Network (WPAN) applications (including RFID and UWB). In some embodiments, each antenna 435 may receive signals or information specific and/or exclusive to itself. In other embodiments, each antenna 435 may receive signals or information not specific or exclusive to itself.

In some embodiments, one or more sensors 150-*a* (e.g., motion, proximity, smoke, light, glass break, door, window, carbon monoxide, and/or another sensor) may connect to some element of system 400 via a network using one or more wired and/or wireless connections.

In some embodiments, the user interface module 425 may include an audio device, such as an external speaker system, an external display device such as a display screen, and/or an input device (e.g., remote control device interfaced with the user interface module 425 directly and/or through I/O controller module 420).

One or more buses 440 may allow data communication between one or more elements of apparatus 205-*b* (e.g., processor module 405, memory 410, I/O controller module 420, user interface module 425, etc.).

The memory 410 may include random access memory (RAM), read only memory (ROM), flash RAM, and/or other types. The memory 410 may store computer-readable, computer-executable software/firmware code 415 including instructions that, when executed, cause the processor module 405 to perform various functions described in this disclosure (e.g., determine sleep state of a person, determine sleep disturbance of the person, track health status of the person, etc.). Alternatively, the software/firmware code 415 may not be directly executable by the processor module 405 but may cause a computer (e.g., when compiled and executed) to perform functions described herein. Alternatively, the computer-readable, computer-executable software/firmware code 415 may not be directly executable by the processor module 405 but may be configured to cause a computer (e.g., when compiled and executed) to perform functions described herein. The processor module 405 may include an intelligent hardware device, e.g., a central processing unit (CPU), a microcontroller, an application-specific integrated circuit (ASIC), etc.

In some embodiments, the memory 410 can contain, among other things, the Basic Input-Output system (BIOS) which may control basic hardware and/or software operation such as the interaction with peripheral components or devices. For example, the monitoring module 215-*b* to implement the present systems and methods may be stored within the system memory 410. Applications resident with system 400 are generally stored on and accessed via a non-transitory computer readable medium, such as a hard disk drive or other storage medium. Additionally, applications can be in the form of electronic signals modulated in accordance with the application and data communication technology when accessed via a network interface (e.g., transceiver module 430, one or more antennas 435, etc.).

Many other devices and/or subsystems may be connected to one or may be included as one or more elements of system 400 (e.g., entertainment system, computing device, remote cameras, wireless key fob, wall mounted user interface device, cell radio module, battery, alarm siren, door lock, lighting system, thermostat, home appliance monitor, utility equipment monitor, heart rate monitor, breathing monitor, and so on). In some embodiments, all of the elements shown in FIG. 4 need not be present to practice the present systems and methods. The devices and subsystems can be interconnected in different ways from that shown in FIG. 4. In some embodiments, an aspect of some operation of a system, such as that shown in FIG. 4, may be readily known in the art and are not discussed in detail in this application. Code to implement the present disclosure can be stored in a non-transitory computer-readable medium such as one or more of system memory 410 or other memory. The operating system provided on I/O controller module 420 may be iOS®, ANDROID®, MS-DOS®, MS-WINDOWS®, OS/2®, UNIX®, LINUX®, or another known operating system.

The transceiver module 430 may include a modem configured to modulate the packets and provide the modulated packets to the antennas 435 for transmission and/or to demodulate packets received from the antennas 435. While the control panel or control device (e.g., 205-*b*) may include a single antenna 435, the control panel or control device (e.g., 205-b) may have multiple antennas 435 capable of concurrently transmitting and/or receiving multiple wireless transmissions.

The apparatus 205-b may include a monitoring module 215-b, which may perform the functions described above for the monitoring module 215, 215-a of apparatus 205 of FIGS. 2 and 3.

Figure 5:
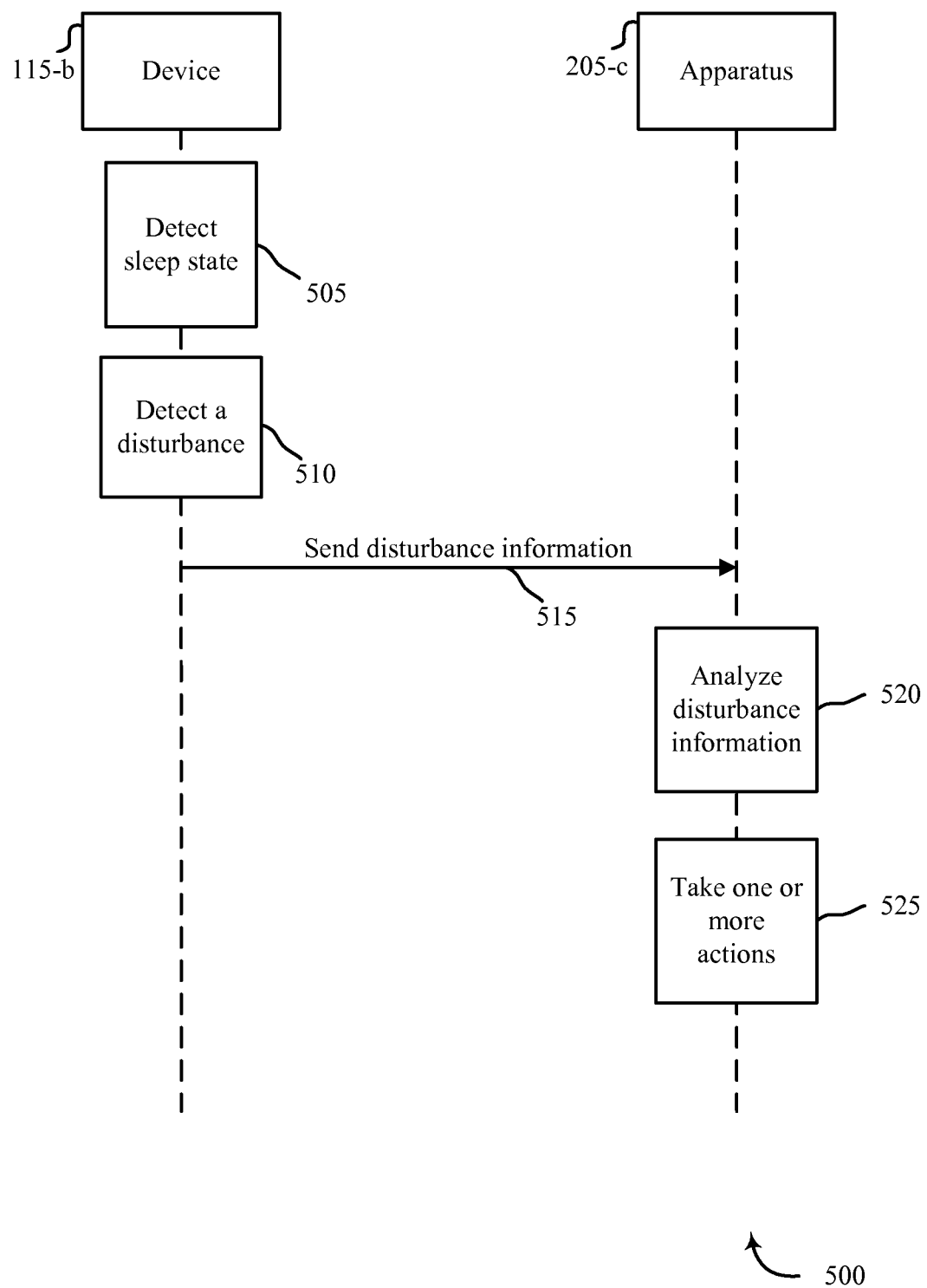
FIG. 5 shows a swim diagram relating to a security and/or an automation system, in accordance with various aspects of this disclosure

FIG. 5 shows a swim diagram 500 for use in smart monitoring systems, in accordance with various examples. The diagram 500 may include an apparatus 205-c, which may be an example of the control panels 105 of FIG. 1. Apparatus 205-c may also be an example of one or more aspects of apparatus 205, 205-a, and/or 205-b of FIGS. 2-4. The diagram 500 may additionally include a device 115-b, which may be an example of the device 115, 115-a and/or a sensor or group of sensors 150, 150-a of FIGS. 1 and/or 4.

The device 115-b may detect a sleep state 505 of a person. The device 115-b may determine the sleep state by detecting heart rate, breathing functions, and/or motion of a person in a sleeping apparatus such as a crib, bed, or the like. Once the device 115-b detects a sleep state, the device 115-b may monitor vital signs and environmental conditions of the person. In some embodiments, the device 115-b may detect a disturbance 510 in the sleep state status of the person. If a disturbance is detected, the device 115-b may send the disturbance information to the apparatus 205-c. The apparatus 205-c may analyze the disturbance information 520 to determine a state of the person. The state of the person may be one of multiple states requiring attention. For example, the person, which may be a child, may be in an emergency state, the child may require feeding, changing, comforting. A noise, such as a dog barking, a car horn, or the like may have disturbed the sleep and the child may require comforting. The child may be fussing in its sleep and may require a moment or two to relax and self-soothe. Depending on the state, the apparatus 205-c may take one or more actions 525. The actions may include notifying emergency personnel of an emergency situation, starting a timer, recording decibel level of crying, alerting a supervisory person, or the like.

Figure 6:
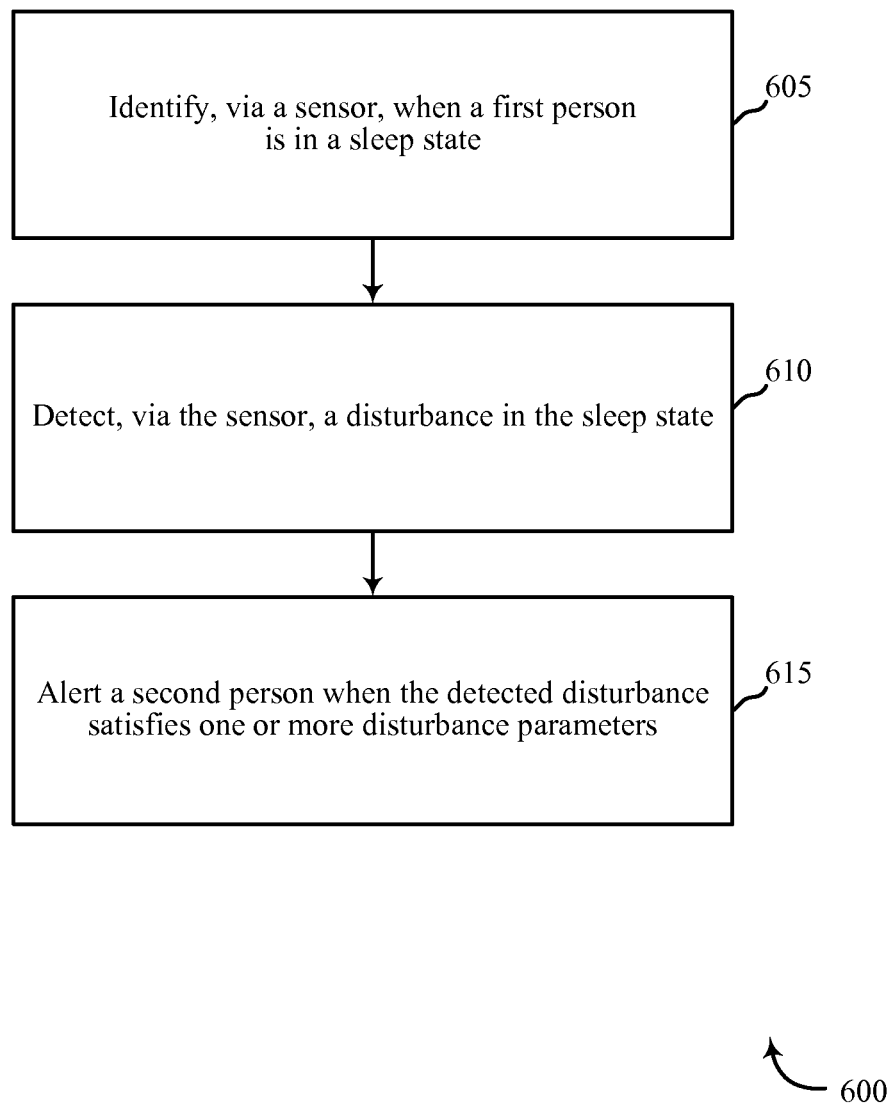
FIG. 6 is a flow chart illustrating an example of a method relating to a security and/or an automation system, in accordance with various aspects of this disclosure.

FIG. 6 is a flow chart illustrating an example of a method 600 for monitoring sleep states of persons, in accordance with various aspects of the present disclosure. For clarity, the method 600 is described below with reference to aspects of one or more of the monitoring module 215 described with reference to FIGS. 1-3, and/or aspects of one or more of the apparatus 205 described with reference to FIGS. 1-5. In some examples, an apparatus may execute one or more sets of codes to control the functional elements of the monitoring module 215 to perform the functions described below. Additionally or alternatively, the apparatus and/or control panel may perform one or more of the functions described below using special-purpose hardware.

At block 605, the method 600 may include identifying, via a sensor, when a first person is in a sleep state. The sensor may be proximate the first person, which may be a child. For example, the sensor may be a wearable device. The sensor may additionally be proximate a sleep location of the first person, such as a bassinet, bed, crib, mobile crib, hammock, and the like. The sensor may be programmed to detect multiple different modes such as motion, breathing, heart rate, brain functionality, noise, and the like. If the sensor detects steady breathing, steady heart rate, lack of motion, and the like, the person may be in a sleep state.

At block 610, the method 600 may include detecting, via the sensor, a disturbance in the sleep state. Once a person is determined to be in a sleep state, the sensor may watch for disturbances in the sleep state. The disturbances may be external and/or internal. For example, external disruptions may include noise disruptions, light disruptions, motion disruptions, and the like. The disturbances may also be internal to the person, such as a dream, hunger or thirst, a soiled diaper, hot, cold, fussy, sick, teething, and the like.

The operation(s) at blocks 605 and 610 may be performed using the detection module 305 described with reference to FIG. 3.

At block 615, the method 600 may include alerting a second person when the detected disturbance satisfies one or more disturbance parameters. The disturbance parameters may include emergency parameters, attention minimums, predetermined time periods for crying or fussiness, body temperature (if the child is sick), and the like. The disturbance parameters may be stated in the alert to the second person. The second person may be a parent, supervisory person, or caregiver. The alert may consist of a text message, audio message, an automation system alert, and the like. The alert may include a severity factor. The severity factor may be listed in the body of the message or may be communicated in the delivery medium. For example, an emergency situation may result in a notification over a speaker system in the automation system. The message may additionally result in a phone call to a person who may be away from the residence. The method 600 may continue to dial the person until an answer is achieved.

The operation(s) at block 615 may be performed using the action module 315 described with reference to FIG. 3.

Thus, the method 600 may provide monitoring a sleep state of a person relating to automation/security systems. It should be noted that the method 600 is just one implementation and that the operations of the method 600 may be rearranged or otherwise modified such that other implementations are possible.

Figure 7:
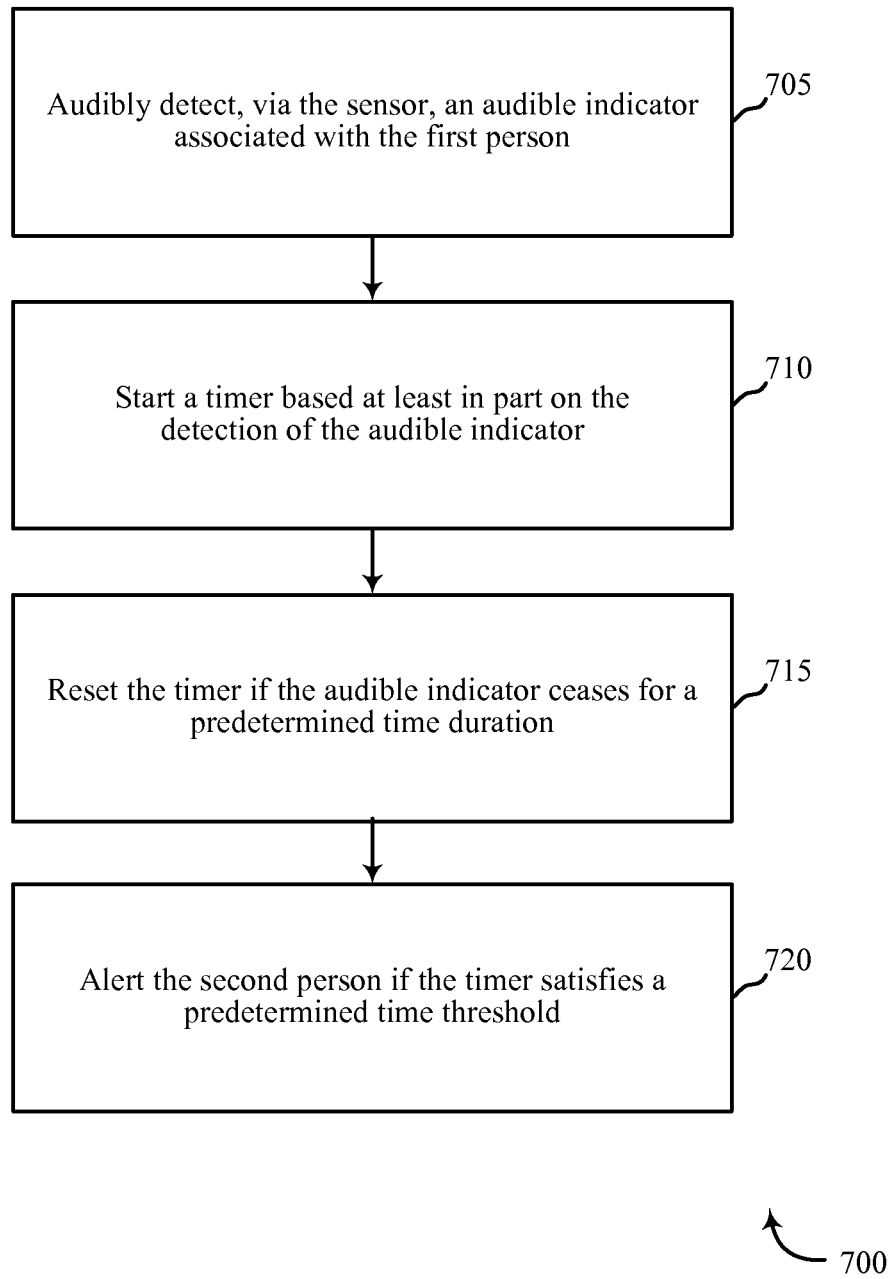
FIG. 7 is a flow chart illustrating an example of a method relating to a security and/or an automation system, in accordance with various aspects of this disclosure.

FIG. 7 is a flow chart illustrating an example of a method 700 for monitoring sleep states of persons, in accordance with various aspects of the present disclosure. For clarity, the method 700 is described below with reference to aspects of one or more of the monitoring module 215 described with reference to FIGS. 1-3, and/or aspects of one or more of the apparatus 205 described with reference to FIGS. 1-5. In some examples, an apparatus may execute one or more sets of codes to control the functional elements of the monitoring module 215 to perform the functions described below. Additionally or alternatively, the apparatus and/or control panel may perform one or more of the functions described below using special-purpose hardware.

At block 705, the method 700 may include audibly detecting, via a sensor, an audible indicator associated with the first person. The audible indicator may be a person crying, such as a small child. It may also consist of a person calling for help, screaming (as in a dream state), or the like.

The operation(s) at block 705 may be performed using the detection module 305 described with reference to FIG. 3.

At block 710, the method 700 may include starting a timer based at least in part on the detection of the audible indicator. The timer may begin at the moment the noise is detected. At block 715, the method 700 may include resetting the timer if the audible indicator ceases for a predetermined time duration. For example, the child may have been disturbed during a sleep state but may be self-soothing to return to a sleep state. This may take a predetermine time period prior to alerting a caregiver, which may allow the child to return to the sleep state. Therefore, if the noise ceases for a predetermined time duration, it may be concluded that the child returned to sleep.

At block 720, the method 700 may include alerting the second person if the timer satisfies a predetermined time threshold. In some instances, the child (e.g. first person) may not settle back into a sleep state. Instead, the child may continue to cry or audibly request assistance. If the child continues after a predetermined time period, the child may require adult assistance to return to a sleep state. This may result in the second person, maybe an adult, being alerted to the status of the child. The alert may contain information pertaining to a status of the child, such as duration of the crying, decibel level of noise, predicted needs of the child, and the like.

The operation(s) at blocks 710, 715 and 720 may be performed using the action module 315 described with reference to FIG. 3.

Thus, the method 700 may provide for monitoring a sleep state of a person relating to automation/security systems. It should be noted that the method 700 is just one implementation and that the operations of the method 700 may be rearranged or otherwise modified such that other implementations are possible.

Figure 8:
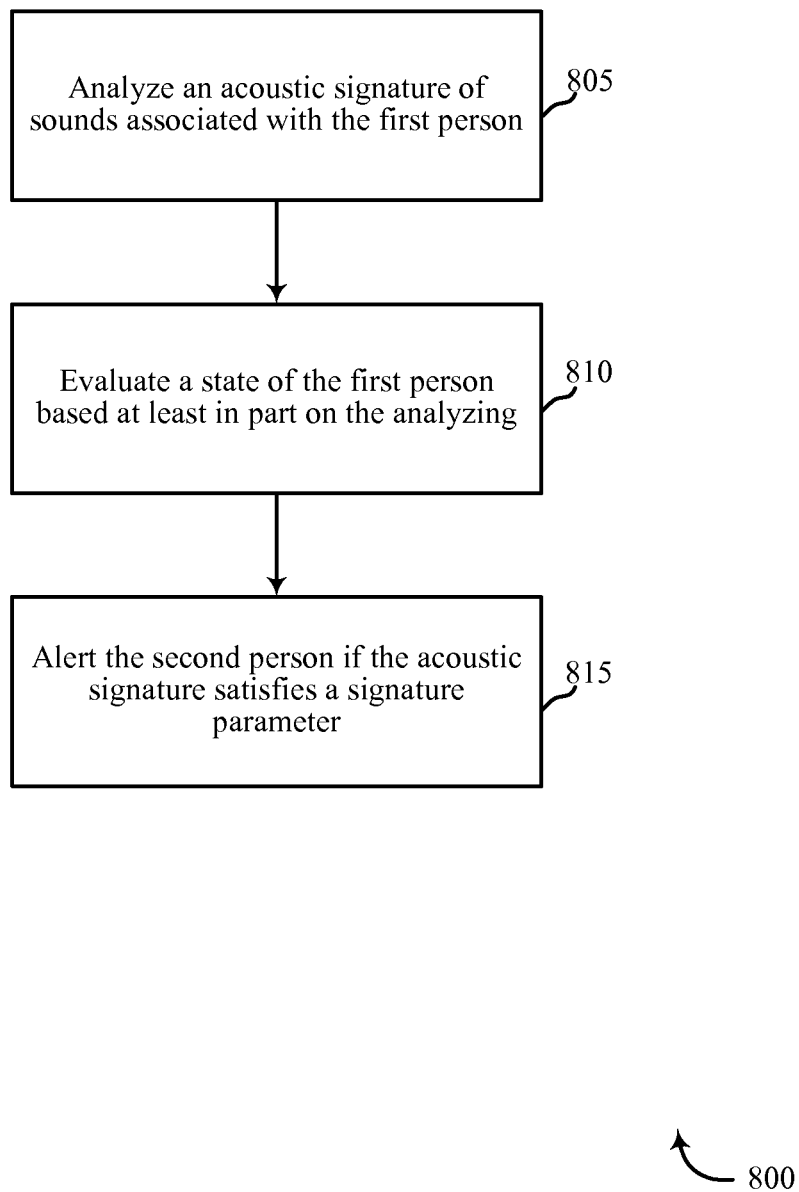
FIG. 8 is a flow chart illustrating an example of a method relating to a security and/or an automation system, in accordance with various aspects of this disclosure.

FIG. 8 is a flow chart illustrating an example of a method 800 for monitoring sleep states of persons, in accordance with various aspects of the present disclosure. For clarity, the method 800 is described below with reference to aspects of one or more of the monitoring module 215 described with reference to FIGS. 1-3, and/or aspects of one or more of the apparatus 205 described with reference to FIGS. 1-5. In some examples, an apparatus may execute one or more sets of codes to control the functional elements of the monitoring module 215 to perform the functions described below. Additionally or alternatively, the apparatus and/or control panel may perform one or more of the functions described below using special-purpose hardware.

At block 805, the method 800 may include analyzing an acoustic signature of sounds associated with the first person. This may include recording the first person when the state of the first person is known. For example, analyzing the acoustic signature may include comparing the acoustic signature to known acoustic signatures of the first person. For example, an acoustic recording of the first person may be recorded when the person is identified as hungry, tired, fussy, in pain, distressed, and the like. If the method 800 detects an audible output from the first person, the method 800 may record the audible output and compare it to known acoustic signatures.

At block 810, the method 800 may include evaluating a state of the first person based at least in part on the analyzing. By comparing the acoustic signatures, the method 800 may determine, with a near certainty, the state of the first person. In some instances, the method 800 may use other information, in addition to an acoustic signature, to determine and/or confirm a state of the first person. For example, additional sensor information may indicate a loud noise woke a sleeping child, or that a person may be overheating or may be cold. This information may supplement and/or strengthen the evaluation.

The operation(s) at blocks 805, 810 may be performed using the evaluation module 310 described with reference to FIG. 3.

At block 815, the method 800 may include alerting the second person if the acoustic signature satisfies a signature parameter. For example, the signature parameter may include acoustic signatures relating to temperature fluctuations, noise disturbances, hunger, pain, and the like. If the signature parameter threshold is satisfied, the second person may receive an alert. The alert may detail the predicted state of the first person and actions which may be taken. In some embodiments, if the first person, e.g. a child, is merely fussy due to a dream and the acoustic signature has not reached a distress level, the second person may not be notified.

The operation(s) at block 815 may be performed using the action module 315 described with reference to FIG. 3.

Thus, the method 800 may provide for monitoring a sleep state of a person relating to automation/security systems. It should be noted that the method 800 is just one implementation and that the operations of the method 800 may be rearranged or otherwise modified such that other implementations are possible.

In some examples, aspects from two or more of the methods 600, 700, 800 may be combined and/or separated. It should be noted that the methods 600, 700, 800 are just example implementations, and that the operations of the methods 600, 700, 800 may be rearranged or otherwise modified such that other implementations are possible.

The detailed description set forth above in connection with the appended drawings describes examples and does not represent the only instances that may be implemented or that are within the scope of the claims. The terms "example" and "exemplary," when used in this description, mean "serving as an example, instance, or illustration," and not "preferred" or "advantageous over other examples." The detailed description includes specific details for the purpose of providing an understanding of the described techniques. These techniques, however, may be practiced without these specific details. In some instances, known structures and apparatuses are shown in block diagram form in order to avoid obscuring the concepts of the described examples.

Information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative blocks and components described in connection with this disclosure may be implemented or performed with a general-purpose processor, a digital signal processor (DSP), an ASIC, an FPGA or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, and/or state machine. A processor may also be implemented as a combination of computing devices, e.g., a combination of a DSP and a microprocessor, multiple microprocessors, one or more microprocessors in conjunction with a DSP core, and/or any other such configuration.

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope and spirit of the disclosure and appended claims. For example, due to the nature of software, functions described above can be implemented using software executed by a processor, hardware, firmware, hardwiring, or combinations of any of these. Features implementing functions may also be physically located at various positions, including being distributed such that portions of functions are implemented at different physical locations.

As used herein, including in the claims, the term "and/or," when used in a list of two or more items, means that any one of the listed items can be employed by itself, or any combination of two or more of the listed items can be employed. For example, if a composition is described as containing components A, B, and/or C, the composition can contain A alone; B alone; C alone; A and B in combination; A and C in combination; B and C in combination; or A, B, and C in combination. Also, as used herein, including in the claims, "or" as used in a list of items (for example, a list of items prefaced by a phrase such as "at least one of" or "one or more of") indicates a disjunctive list such that, for example, a list of "at least one of A, B, or C" means A or B or C or AB or AC or BC or ABC (i.e., A and B and C).

In addition, any disclosure of components contained within other components or separate from other components should be considered exemplary because multiple other architectures may potentially be implemented to achieve the same functionality, including incorporating all, most, and/or some elements as part of one or more unitary structures and/or separate structures.

Computer-readable media includes both computer storage media and communication media including any medium that facilitates transfer of a computer program from one place to another. A storage medium may be any available medium that can be accessed by a general purpose or special purpose computer. By way of example, and not limitation, computer-readable media can comprise RAM, ROM, EEPROM, flash memory, CD-ROM, DVD, or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, include compact disc (CD), laser disc, optical disc, digital versatile disc (DVD), floppy disk, and Blu-ray disc where disks usually reproduce data magnetically, while discs reproduce data optically with lasers. Combinations of the above are also included within the scope of computer-readable media.

The previous description of the disclosure is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not to be limited to the examples and designs described herein but is to be accorded the broadest scope consistent with the principles and novel features disclosed.

This disclosure may specifically apply to security system applications. This disclosure may specifically apply to automation system applications. In some embodiments, the concepts, the technical descriptions, the features, the methods, the ideas, and/or the descriptions may specifically apply to security and/or automation system applications. Distinct advantages of such systems for these specific applications are apparent from this disclosure.

The process parameters, actions, and steps described and/or illustrated in this disclosure are given by way of example only and can be varied as desired. For example, while the steps illustrated and/or described may be shown or discussed in a particular order, these steps do not necessarily need to be performed in the order illustrated or discussed. The various exemplary methods described and/or illustrated here may also omit one or more of the steps described or illustrated here or include additional steps in addition to those disclosed.

Furthermore, while various embodiments have been described and/or illustrated here in the context of fully functional computing systems, one or more of these exemplary embodiments may be distributed as a program product in a variety of forms, regardless of the particular type of computer-readable media used to actually carry out the distribution. The embodiments disclosed herein may also be implemented using software modules that perform certain tasks. These software modules may include script, batch, or other executable files that may be stored on a computer-readable storage medium or in a computing system. In some embodiments, these software modules may permit and/or instruct a computing system to perform one or more of the exemplary embodiments disclosed here.

This description, for purposes of explanation, has been described with reference to specific embodiments. The illustrative discussions above, however, are not intended to be exhaustive or limit the present systems and methods to the precise forms discussed. Many modifications and variations are possible in view of the above teachings. The embodiments were chosen and described in order to explain the principles of the present systems and methods and their practical applications, to enable others skilled in the art to utilize the present systems, apparatus, and methods and various embodiments with various modifications as may be suited to the particular use contemplated.

What is claimed is:

1. A method for operating a security and/or automation system, comprising:
   identifying, via a sensor, when a first person is in a sleep state;
   detecting, via the sensor, a disturbance in the sleep state;
   recording data during a time period associated with the detected disturbance;
   analyzing the recorded data to identify a cause of the detected disturbance;
   comparing the identified cause with one or more parameters; and
   alerting a second person when the cause satisfies one or more parameters based at least in part on the comparison.

2. The method of claim 1, wherein detecting the disturbance in the sleep state further comprises:
   audibly detecting, via the sensor, an audible indicator associated with the first person; and
   starting a timer based at least in part on the detection of the audible indicator.

3. The method of claim 2, further comprising:
   resetting the timer if the audible indicator ceases for a predetermined time duration.

4. The method of claim 2, further comprising:
   alerting the second person if the timer satisfies a predetermined time threshold.

5. The method of claim 2, further comprising:
   determining when the audible indicator satisfies a predetermined decibel threshold; and
   alerting the second person based at least in part on the determining.

6. The method of claim 1, further comprising:
identifying a location of the first person; and
deactivating one or more household alerts based at least in part on the identified location.

7. The method of claim 1, further comprising:
analyzing an acoustic signature of sounds associated with the first person;
evaluating a state of the first person based at least in part on the analyzing; and
alerting the second person if the acoustic signature satisfies a signature parameter.

8. The method of claim 1, wherein the recorded data comprises video data and audio data of the first person when the sleep state is disrupted; and the method further comprising:
saving the video data and the audio data.

9. The method of claim 1, further comprising:
tracking vital signs of the first person while the first person is in the sleep state; and
immediately alerting emergency personnel when at least one of the vital signs satisfies an emergency threshold.

10. The method of claim 9, further comprising:
saving video data, audio data, and sensor information for a predetermined time period, the predetermined time period comprising a first time period before the emergency threshold is satisfied until a second time period after the emergency threshold is satisfied.

11. The method of claim 1, further comprising:
activating a soothing mechanism proximate a location of the first person when the sleep state is disturbed.

12. The method of claim 1, wherein detecting the disturbance in the sleep state further comprises:
detecting when a current state of the first person requires a change.

13. The method of claim 1, wherein the sensor comprises at least one of a bed sensor, an audio sensor, a video sensor, a motion sensor, a camera, a microphone, a light sensor, or a combination thereof.

14. An apparatus for security and/or automation systems, comprising:
a processor;
memory in electronic communication with the processor; and
instructions stored in the memory, the instructions being executable by the processor to:
identify, via a sensor, when a first person is in a sleep state;
detect, via the sensor, a disturbance in the sleep state;
record data during a time period associated with the disturbance;
analyze the data to identify a cause of the disturbance;
compare the cause with one or more parameters; and alert a second person when the cause satisfies one or more parameters based at least in part on the comparison.

15. The apparatus of claim 14, wherein the instructions are further executable by the processor to:
track vital signs of the first person while the first person is in the sleep state; and
immediately alert emergency personnel when at least one of the vital signs satisfies an emergency threshold.

16. The apparatus of claim 14, wherein the instructions are further executable by the processor to:
audibly detect, via the sensor, an audible indicator associated with the first person; and
start a timer based at least in part on the detection of the audible indicator.

17. The apparatus of claim 16, wherein the instructions are further executable by the processor to:
reset the timer if the audible indicator ceases for a predetermined time duration.

18. A non-transitory computer-readable medium storing computer-executable code, the code executable by a processor to:
identify, via a sensor, when a first person is in a sleep state;
detect, via the sensor, a disturbance in the sleep state;
record data during a time period associated with the disturbance;
analyze the data to identify a cause of the disturbance;
compare the cause with one or more parameters; and
alert a second person when the cause satisfies one or more parameters based at least in part on the comparison.

19. The computer-readable medium of claim 18, wherein the code is further executable by the processor to:
track vital signs of the first person while the first person is in the sleep state; and
immediately alert emergency personnel when at least one of the vital signs satisfies an emergency threshold.

20. The computer-readable medium of claim 18, wherein the code is further executable by the processor to:
audibly detect, via the sensor, an audible indicator associated with the first person; and
start a timer based at least in part on the detection of the audible indicator.

* * * * *